US006529270B1

(12) United States Patent
Bills

(10) Patent No.: US 6,529,270 B1
(45) Date of Patent: Mar. 4, 2003

(54) APPARATUS AND METHOD FOR DETECTING DEFECTS IN THE SURFACE OF A WORKPIECE

(75) Inventor: Richard Earl Bills, Tucson, AZ (US)

(73) Assignee: ADE Optical Systems Corporation, Charlotte, NC (US)

( * ) Notice: Subject to any disclaimer, the term of this patent is extended or adjusted under 35 U.S.C. 154(b) by 0 days.

(21) Appl. No.: 09/538,707

(22) Filed: Mar. 30, 2000

Related U.S. Application Data
(60) Provisional application No. 60/127,144, filed on Mar. 31, 1999.

(51) Int. Cl.$^7$ .............................................. G01N 21/88
(52) U.S. Cl. .................................................. 356/237.2
(58) Field of Search ........................... 356/237.2, 237.3, 356/237.4, 237.5

(56) References Cited

U.S. PATENT DOCUMENTS

| 5,712,701 A | | 1/1998 | Clementi et al. |
| 5,715,051 A | * | 2/1998 | Luster ..................... 356/237.2 |
| 5,864,394 A | | 1/1999 | Jordan, III et al. |

FOREIGN PATENT DOCUMENTS

| DE | 44 00 868 A1 | 7/1995 |
| JP | 06258250 A | 9/1994 |

OTHER PUBLICATIONS

George R. Cooper and Claire D. McGillim, *Modern Communication & Spread Spectrum*, McGraw Hill, New York, 1986, pp. 82–91.

* cited by examiner

Primary Examiner—Richard A. Rosenberger
(74) Attorney, Agent, or Firm—Alston & Bird LLP

(57) ABSTRACT

The present invention provides apparatus and methods for scanning a workpiece for defects with increased resolution and sensitivity relative to conventional workpiece inspection systems. Specifically, the apparatus and methods of the present invention repeatedly scan different portions of the workpiece with an optical beam that forms a scan region on the surface of the workpiece having in-scan and cross-scan dimensions. The in-scan dimension of the scan region is parallel to the direction with which the optical beam is scanned, and the cross-scan dimension is in a direction that is generally perpendicular to the direction in which the optical beam is scanned. The apparatus and methods of the present invention filter the signal reflected from the surface of the workpiece in the cross-scan direction using a cross-scan filter. As such, the method and apparatus of the present invention effectively remove a significant portion of the noise in the reflected signals used for detecting for defects in the workpiece. Further, in some embodiments, the apparatus and method also filter the reflected signal in the in-scan direction using an in-scan filter. By filtering the reflected signals in either a cross-scan or both a cross-scan and in-scan directions, the apparatus and methods of the present invention remove noise from the reflected signals, thereby increasing the sensitivity and resolution of the workpiece inspection device.

48 Claims, 11 Drawing Sheets

APPARATUS AND METHOD FOR DETECTING DEFECTS IN THE SURFACE OF A WORKPIECE

CROSS-REFERENCE TO RELATED APPLICATIONS

The present application claims priority from U.S. Provisional Application Serial No. 60/127,144 entitled Signal Processing Method For An Optical Wafer Inspection Device filed Mar. 31, 1999, the contents of which are incorporated herein by reference.

FIELD OF THE INVENTION

The present invention relates generally to the inspection of the surface of a workpiece for defects. More particularly, the present invention relates to an apparatus and method that scan the surface of a workpiece with an optical beam and process the optical signal reflected and detected from the surface of the workpiece prior to determining from the reflected optical signal whether the workpiece includes defects, thereby increasing the sensitivity of the inspection.

BACKGROUND OF THE INVENTION

For most semiconductor microelectronic applications, an important factor is the feature size of devices located on a silicon integrated circuit die. These devices include transistors, such as MOSFET's, metallization paths, as well as capacitors and resistors. In particular, for most applications, the smaller the size of the semiconductive device the better. Smaller device geometry enables higher transistor switching speeds due to smaller junction capacitance. It also enables the development of digital circuits with greater processing power and complexity. Just a few years ago, the typical feature size for a typical semiconductive transistor was approximately 300 nanometers (nm). However, more recently the feature size has been reduced to 180 nm, while some semiconductive transistors are now being manufactured with dimensions of 130 nm.

Although the miniaturization of semiconductor devices is typically advantageous, this reduction in size has imposed some problems in the manufacturing of these devices. Specifically, semiconductive devices are manufactured from crystalline silicon wafers that have been grown, sliced into wafers, and polished. Although the methods for creating these wafers and preparing them for semiconductor manufacture are quite advanced, contaminant particles may be introduced onto the surface of the wafer and/or contaminants or surface defects may be present in the wafer. These contaminants and/or defects, if large in dimension relative to the semiconductive device to be manufactured from the wafer, may result in device defects and reduced production yields. As such, as the size of semiconductive devices and their associated components are reduced, contaminants and defects of smaller sizes, which were once negligible, have become problematic.

For example, if a semiconductive device has dimensions of approximately 300 nm, a contaminant or defect having a dimension of 60 nm is typically negligible. However, as the feature size is reduced to 180 nm, this same defect may cause a defect in the manufactured device.

As a result of the problems described above, more stringent requirements have been placed on inspection devices used to detect defects in silicon wafers. The Semiconductor Equipment Manufacturing Industry consortium (SEMI) is an organization that defines defect sensitivity requirements for silicon wafer inspection devices. The sensitivity is typically defined in terms of the scanner's ability to detect a polystyrene latex sphere (PSL) of a selected diameter. As an example of the increased sensitivity requirements, SEMI has recently released guidelines requiring that an inspection device maintain reliable detection capability of a 65 nm PSL defect for a 130 nm device geometry.

These increased sensitivity requirements have been problematic for many conventional silicon wafer inspection devices. Specifically, many conventional silicon wafer inspection devices use laser-based scanners and photomultiplier-based optical detectors to inspect the surface of silicon wafers for defects. While optical inspection systems have been capable of detecting 100 nm defects on silicon wafers, their performance is limited by quantum-mechanical shot noise. This noise is caused by the statistical probability associated with detecting the photons received from the scattered light that is reflected from the wafer surface. This susceptibility to noise limits the inspection system's sensitivity to small particles that can cause device defects. In particular, the signal produced by particles decreases non-linearly with decreasing particle size.

At least one problem with the introduction of shot noise in silicon wafer inspection devices is illustrated in FIG. 1. FIG. 1 illustrates a portion of a conventional silicon wafer inspection system. This conventional silicon wafer inspection system 10 includes a light source 12 such as laser for directing an optical beam B toward the surface S of a workpiece W. The silicon wafer inspection system also includes a dark channel detector system 18 that may include several individual detectors for detecting scattered light reflected from the surface of the workpiece. The conventional silicon wafer inspection system also includes a light channel detector 20 positioned at an angle β that corresponds to, i.e., typically equal to, the angle β the beam makes with respect to the workpiece. The light channel detector detects specularly reflected light from the surface of the workpiece.

Importantly, the silicon wafer inspection device also includes a deflector 14 and an optical lens 16. The deflector and lens are positioned to receive the optical beam and deflect the beam so as to form a scan region 22 on the surface the workpiece. The scan region is defined by an in-scan dimension 24 that relates to the scan path of the light beam. Specifically, the scan path is the sweep of the optical beam through an angle cc controlled by the deflector. Further, the scan region includes a cross-scan dimension 26 that is associated with the width of the beam.

In operation, the workpiece or the laser is usually moved in relation to the optical beam such that the laser scans either all or a substantial portion of the surface of the workpiece. As the workpiece is scanned, the dark and light channel detectors receive optic signals reflected from the surface of the workpiece. These optic signals are provided to a signal processing device 28 for determining whether the workpiece includes defects.

As stated previously, a problem associated with many of these conventional systems is the introduction of shot noise into the dark channels of the silicon-wafer inspection system. This noise can overshadow small defects in the workpiece, thereby decreasing the sensitivity of the silicon-wafer inspection device. For example, FIG. 2 is a plot of the data signal received by a photomultiplier dark channel detector from a scan of a section of a workpiece by a conventional inspection device. This section of the workpiece includes a 100 nm PSL defect that is illustrated in the center of the scan by peak 30. Importantly, as illustrated by the plot, the optical signal received by the dark channel detector includes a considerable amount of noise that may overshadow smaller defects in the workpiece. Specifically, the amplitude of the signal generated by a defect is typically related to the diameter D of the defect by following equation:

Amplitude of Defect Diameter$^6$

As such, as the diameter of the defect decreases, the amplitude of the signal created by the defect decreases dramatically, thereby making the detection of smaller defects in a workpiece more problematic in a noisy inspection device.

In light of the problems associated with the introduction of signal noise in the dark and light channel detectors, silicon-wafer inspection systems have been developed to filter at least some of the noise from the received signals. These conventional inspection devices use signal filtering techniques to reduce the amount of noise in the optical signal received from the silicon wafer. These filtering techniques advantageously increase the sensitivity of the inspection device. However, these conventional inspection devices may not provide adequate filtering of the signal to reliably detect defects in the range of 65 nm as required by the SEMI guidelines.

Specifically, these conventional inspection devices filter the optical signal in the in-scan direction 24 of the scan region. The in-scan filter located in the signal processing device 28 is typically a conventional analog filter, and as further discussed below, is typically designed to match the light intensity characteristics of the optical beam B, such as a typical Gaussian light intensity distribution. As shown in FIG. 3, the in-scan filter filters the optical signals received by the dark and light channel detectors and effectively reduces the introduction of signal noise. Specifically, as shown in FIG. 3, which illustrates the optical signal received by the dark channel detector after the filter, the signal contains less noise. Further, the peak 30 indicating the defect is much more pronounced relative to the background shot noise.

As illustrated, the wafer inspection device effectively reduces some of the signal noise received by the light and dark channel detectors, thereby making the wafer inspection device more sensitive. However, as illustrated in FIG. 3, the filtered optical signal still includes considerable optical shot noise that may overshadow the optical signals produced by smaller dimensioned defects. As such, it would be desirable to provide an inspection system that has reduced noise to thereby increase the sensitivity of the inspection device.

SUMMARY OF THE INVENTION

A method and apparatus are therefore provided that scan a workpiece for defects with increased resolution and sensitivity relative to conventional techniques. In this regard, the method and apparatus of the present invention repeatedly scan different portions of the workpiece and the reflected signals are filtered in a cross-scan direction, that is, in a direction generally perpendicular to the direction in which the light beam is scanned. As such, the method and apparatus of the present invention effectively remove a significant portion of the noise in the reflected signals by filtering in the cross-scan direction. By appropriately filtering the reflected signals, the method and apparatus of the present invention can also take into account differences in the magnitude of the light that illuminates different portions of the workpiece in the cross-scan direction by filtering the reflected signals in the cross-scan direction in a manner that matches the light intensity distribution. As such, the method and apparatus of the present invention can detect defects in or on the workpiece with greater precision and greater resolution due to the filtering of the reflected signals in the cross-scan direction. Thus, the method and apparatus of the present invention can reliably detect smaller particles or other smaller defects on the surface of a workpiece than conventional defect detection techniques.

According to one advantageous embodiment, the workpiece is initially illuminated by a light source that provides an optical beam having in-scan and cross-scan dimensions defining a scan zone. In particular, each of a plurality of different portions of the workpiece is sequentially illuminated in a predetermined scan direction to thereby define a plurality of scans. As a point of reference, the in-scan dimension of the optical beam extends parallel to the predetermined scan direction and the cross-scan dimension of the optical beam is perpendicular to the predetermined scan direction. At least some of the optical signals that illuminate the workpiece are reflected during each of the scans. The reflected signals are typically received and collected by optical receivers or detectors. A digital data set is then constructed for each scan of the workpiece. The data set for each scan is then filtered, typically by the digital cross-scan filter, in the cross-scan dimension of the optical beam based upon at least one data set corresponding to the optical signals received during another scan. In other words, the data set for one scan is filtered in the cross-scan dimension based upon another data set corresponding to another scan.

In one advantageous embodiment, a data set is constructed for each respective scan that has individual data points representing the optical beam reflected from the workpiece at different respective positions along the scan direction. In order to filter the data set, each data point of the scan is preferably individually filtered based upon a corresponding data point of a data set representing the optical signals received during another scan to thereby filter the data set in the cross-scan dimension of the optical beam.

In a further advantageous embodiment, each of the individual data points of the data set are filtered based on a plurality of other data sets representing the optical signal received during a plurality of respective scans occurring prior to and after the present scan. In this embodiment, the individual data points of the data set of the present scan are individually added to corresponding individual data points of the plurality of data sets corresponding to scans of the workpiece occurring prior to and after the present scan to thereby filter the data set of the respective scan in the cross-scan dimension of the optical beam.

Typically, the workpiece is illuminated with an optical beam having a predetermined light intensity distribution in the cross-scan dimension such that different positions of the workpiece in a respective scan are illuminated with light having different magnitudes in the in-scan and cross-scan dimensions. In order to filter the data set in the cross-scan dimension, the filter must be matched to the light intensity distribution of the optical beam. To match the filter to the optical beam, an adjusted data set is therefore generated for each scan that accounts for the predetermined light intensity distribution of the optical beam in the cross-scan dimension of the optical beam. In particular, the adjusted data set can be generated, typically by the cross-scan filter, by multiplying the individual data points of the data set by a predefined cross-scan coefficient that accounts for the differences in the magnitude of light that illuminates the different positions of the workpiece in the respective scan in the cross-scan dimension.

In addition to multiplying the individual data points of a data set by a predefined cross-scan coefficient such that the filter matches the light density distribution of the optical beam, each data point of the adjusted data set of the respective scan is also filtered in the cross-scan direction. The data points of the adjusted data set are filtered in the cross-scan direction by individually adding each data point of the adjusted data set to corresponding data points of another adjusted data set corresponding to an optical signal received by the receiver during another scan, where the adjusted data set has been adjusted by another predefined cross-scan coefficient. By adding the individual data points of the adjusted data set of the present scan that has been adjusted by a cross-scan coefficient to the individual data points of another adjusted data set of another scan that has been adjusted by another cross-scan coefficient, a filtered data set is created that has been filtered in the cross-scan dimension of the optical beam. In order to further filter the data set in the cross-scan dimension, each data point of the adjusted data set of the present scan is individually added to corresponding data points of a plurality of adjusted data sets that have each been adjusted by predefined cross-scan coefficients.

In one embodiment, the workpiece is illuminated with an optical beam having a predetermined Gaussian light intensity distribution. As such, portions of the workpiece located in a middle portion of the scan are illuminated with light having a greater intensity than portions of the workpiece located on opposite end portions of the scan in the cross-scan dimension. In order to match the cross-scan filter to the light intensity distribution of the optical beam, the individual data points of a data set are multiplied by a predetermined cross-scan coefficient that accounts for the differences in the magnitude of light that illuminates the different positions of the workpiece in the respective scan in the cross-scan direction.

In addition to adjusting the data set of the scan so that the filter is matched to the light intensity distribution of the optical beam, in one embodiment, the data set is also filtered in the cross-scan dimension of the optical beam. In this embodiment, the data set is filtered based on a plurality of data sets corresponding to scans of the workpiece occurring prior to and after the present scan. To match the cross-scan filter, for each of the plurality of scans, an adjusted data set is generated to account for the predetermined Gaussian light intensity distribution of the optical beam in the cross-scan dimension. Each of the adjusted data sets is generated by multiplying the individual data points of each data set by a respective predefined cross-scan coefficient. Data sets representing scans closer in time to the present scan are multiplied by greater scan-coefficient values than the individual data points representing data sets corresponding to scans occurring further in time from the present scan. After each of the plurality of data sets have been adjusted, the present scan is filtered in the cross-scan dimension of the optical beam by adding the corresponding individual data points of the plurality of adjusted data sets corresponding to scans of the workpiece occurring prior to and after the respective scan to the individual data points of the adjusted data set of the present scan.

In addition to filtering the reflected optical signals in a cross-scan direction, the optical signals received during a respective scan can also be filtered in the in-scan dimension of the optical beam, typically by means of an in-scan filter. Like the cross-scan filtering, the in-scan filter is matched to filter the optical signals based on the predetermined light intensity distribution of the optical beam in the in-scan dimension. For example, in instances in which the workpiece is illuminated with an optical beam having a predetermined Gaussian light intensity distribution, the portions of the workpiece located in a middle portion of a scan are illuminated with light having greater intensity than portions of the workpiece located on the opposed end portions of the scan in the in-scan dimension. As such, the in-scan filter is matched to the light intensity distribution of the optical beam, such that the in-scan filter filters the optical signals accordingly.

The method and apparatus of one embodiment of the present invention can also remove optical noise in the scan caused by irregularities in the surface of the workpiece. In this regard, a data set for each respective scan is received, typically by a processor. As described above, the data set has individual data points representing the optical beam reflected from the workpiece at different positions along the scan direction. According to this embodiment, a predetermined number of data points are selected from each of a plurality of respective scans. An average scan is then generated, typically by the processor. The average scan has individual data points representing the average optical beam reflected from the workpiece at different positions along the scan direction for the plurality of scans. Individual data points of the average scan are then subtracted, typically by the processor, from the respective individual data points of each data set for each of the plurality of scans. As such, each data set can be corrected for irregularities in the surface of the workpiece.

The method and apparatus of another embodiment of the present invention can determine whether the workpiece contains a defect. In this embodiment, each data point of the respective scan is compared to a threshold value, typically by means of a processor. Thereafter, portions of the workpiece that have corresponding data points in the scan that are at least as great as the threshold value are identified as potential defects.

The method and apparatus of another embodiment of the present invention can also compensate for consistent variations in the intensity of the optical signal. In this regard, a repetitive or systematic signature data set can be subtracted from the data set that represents the optical signals that reflected from the workpiece at different positions along the scan direction. Typically, the signature data set includes individual data points representing the consistent variations in the intensity of the optical signal. Thus, the resulting data set can more accurately represent any defects in or on the surface of the workpiece.

According to the present invention, the method and apparatus filters the reflected optical signals in the cross-scan dimension and, accordingly, removes noise from the reflected optical signals. In addition, the method and apparatus of the present invention effectively compensates for the predetermined light intensity distribution of the optical beam, such as a predetermined Gaussian light intensity distribution, when filtering the optical signal in the cross-scan dimension. By filtering the reflected optical signals in the cross-scan dimension, the resulting filtered data set more accurately represents defects in or on the surface of the workpiece such that smaller defects can be identified with greater precision than conventional defect detection techniques.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will filly convey the scope of the invention to those skilled in the art. Like numbers refer to like elements throughout.

As described above and in more detail below, the present invention provides apparatus and methods for increasing the sensitivity of a wafer inspection device by filtering the optical signals prior to determining whether the optical signal indicates that the wafer includes defects. Specifically, as described above, at least one conventional wafer inspection system filters the optical signal in an in-scan direction parallel to the direction of the scan of the optical beam. The apparatus and methods of the present invention advantageously increase the sensitivity and resolution of the wafer inspection device by either alternatively or further filtering the optical signal in a cross-scan direction perpendicular to the scan of the optical beam. By filtering the optical signal in a cross-scan direction, the apparatus and methods of the present invention increase the signal-to-noise (SNR) ratio of the optical signal by reducing shot noise. This, in turn, prevents shot noise from overshadowing smaller amplitude signals in the optical signal corresponding to smaller defects in the workpiece.

As used herein, defects shall mean not only physical defects within the workpiece, such as scratches, pits, of the like, but also particles or other foreign objects on or in the surface of the workpiece.

For illustrative purposes, the various apparatus and methods of the present invention are shown and described below in conjunction with the wafer inspection system of U.S. Pat. No. 5,712,701 to Clementi et al. The Clementi '701 patent is assigned to the assignee of the present application, and the contents of this reference are hereby incorporated by reference. Although the apparatus and methods of the present invention are illustrated in conjunction with the inspection system of the Clementi '701 patent, it should be apparent that the apparatus and methods of the present invention can be used either independently or in combination with other inspection systems, if so desired.

Figure 1:
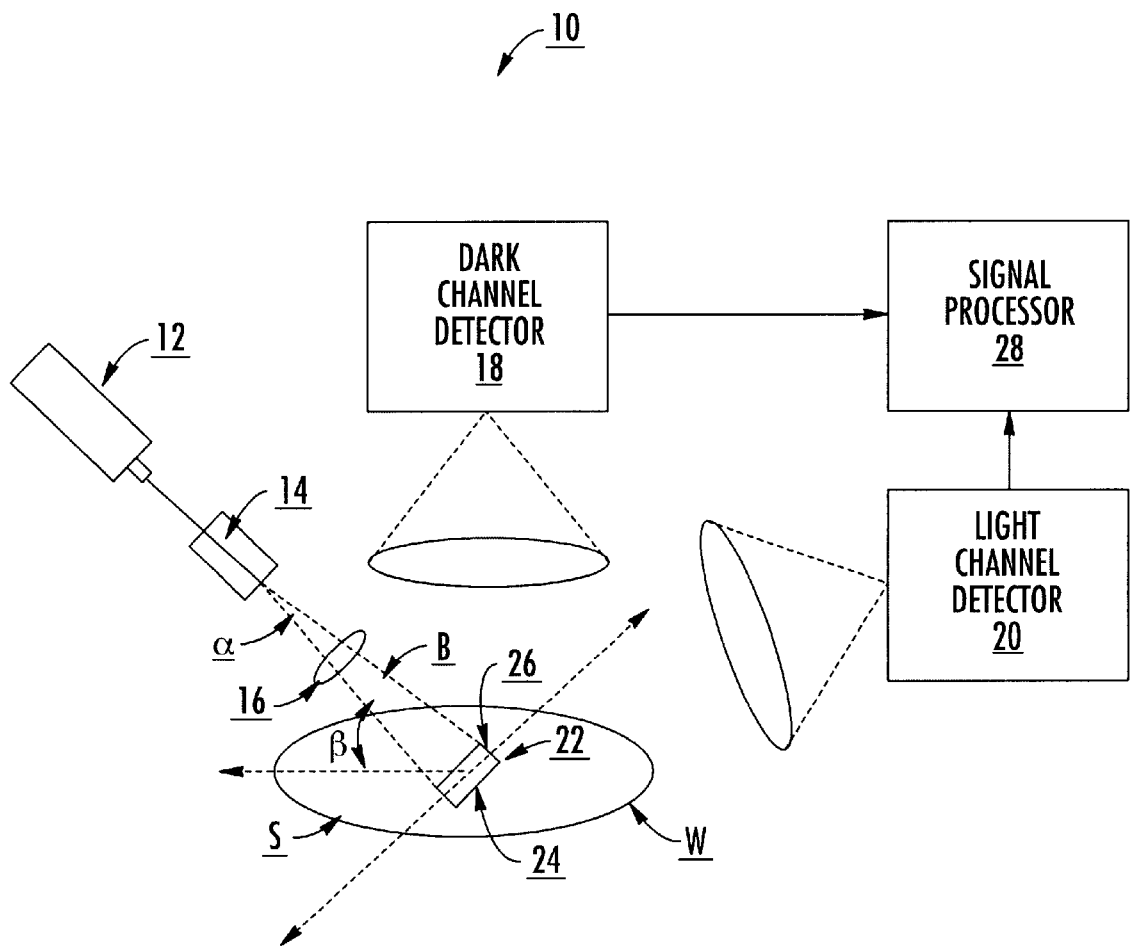
FIG. 1 is a block diagram of a conventional workpiece inspection device that uses optical signals to scan a workpiece for defects.

FIG. 1 depicts many of the components of the wafer inspection system of the Clementi '701 patent in simplified form for illustrative purposes. It must be understood that only the more relevant portions of the wafer inspection device of the Clementi '701 patent are illustrated and that there are other components, such as lenses, beam expanders, stop members, power supplies, processors, controllers, etc. that are used in the wafer inspection device, but are not illustrated in FIG. 1. For more detailed information concerning these components and the operation of the wafer inspection device, reference is made to the Clementi '710 patent.

With reference to FIG. 1, a conventional wafer inspection device with which the apparatus and methods of the present invention may be used is illustrated. The wafer inspection system 10, similar to many other inspection systems, includes a light source 12, such as a laser, for directing an optical beam B toward the surface S of a workpiece W. The silicon wafer inspection system also includes a dark channel detector system 18 that may include several individual detectors for detecting scattered light reflected from the surface of the workpiece at differing angles. For example, in one embodiment, the dark channel detector is a photo multiplier tube (PMT).

The wafer inspection system also includes a light channel detector 20. The light channel detector is positioned at an angle β that corresponds to the angle β the beam makes with respect to the workpiece. The light channel detector detects specular light reflected by the surface of the workpiece due to scratches in the workpiece. The light channel detector may also be a PMT, a quad cell silicon photo diode detector, of the like.

The wafer inspection device also includes a deflector 14 and an optical lens 16. The deflector and lens are positioned to receive the optical beam and deflect the beam B so as to form a scan region 22 on the surface the workpiece. The deflector is typically an acousto-optical (AO) deflector, which dithers the optical beam emitted from the light source such that the optical beam scans in a sweep. The scan region is defined by an in-scan dimension 24, which relates to the scan path of the light beam. Specifically, the scan path is the sweep of the optical beam through an angle α controlled by the deflector. Further, the scan region includes a cross-scan dimension 26 that is associated with the width of the beam. For example, in a typical inspection system, the scan region is 4 millimeters in the in-scan, or scan sweep direction. If the laser spot size is 50 microns (full width at $1/e^2$ level), and β=65 degrees, then the effective width of the sweep will be 118 microns (fall width at $1/e^2$ level) in the cross-scan dimension.

Figure 4:
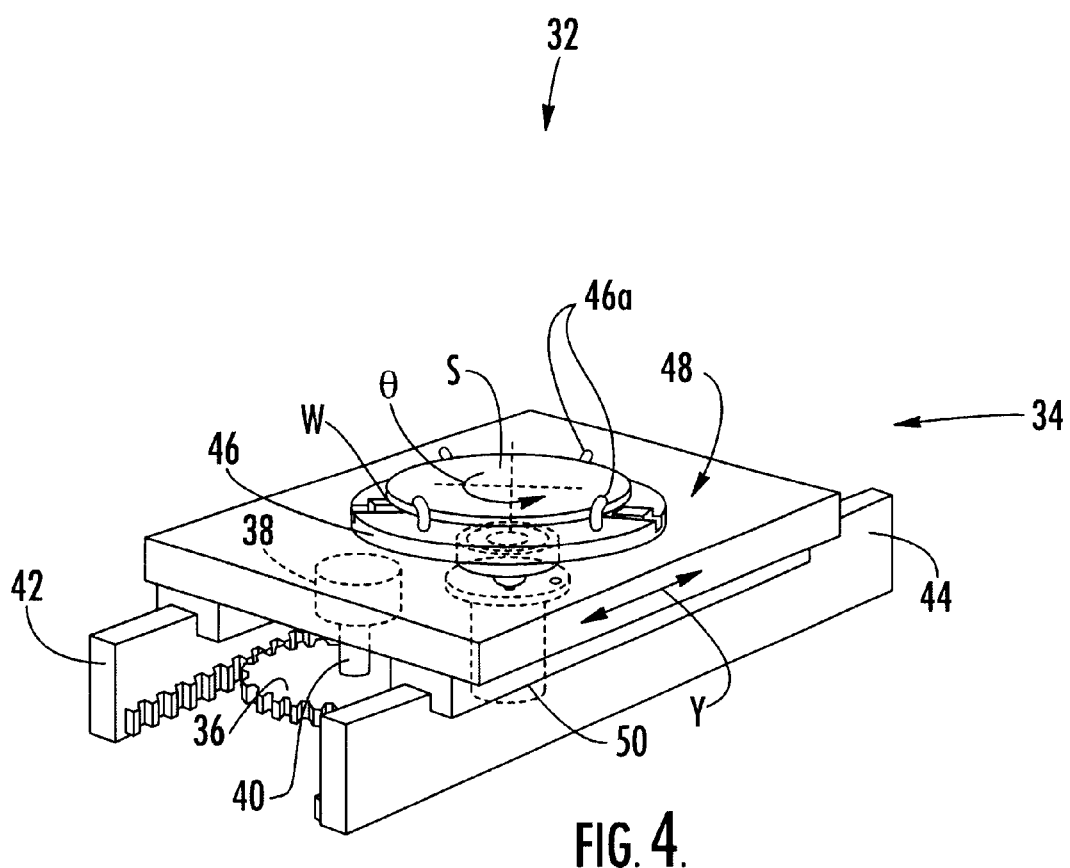
FIG. 4 is a perspective view of a wafer handling device for use in a conventional workpiece inspection device.

With reference to FIG. 4, the inspection device of the Clementi '701 patent also includes a workpiece handling device 32 for holding the workpiece and moving the workpiece relative to the beam B emitted from the light source, such that the light source may scan different portions of the surface of the workpiece. Importantly, the workpiece handling device includes a translational transporter 34 for translationally transporting the workpiece W along a material path P. The translational transporter includes a gear 36, a motor 38 including a shaft 40 arranged for rotating the gear 36, and guides, 42 and 44, with teeth. The motor 38 and gear 36 mounted on the motor shaft 40 form a chuck. The motor of the chuck is preferably mounted to a stage member 46 having a plurality of flanges 46a extending upwardly therefrom, which receives the workpiece W.

The workpiece handling device also includes a rotator 48 associated with the translational transporter 34 and arranged to rotate the workpiece W during translational travel along the material path P. The rotator 48 includes a motor 50 mounted to an underside of the stage member for providing rotation of the wafer mounted thereon at a predetermined speed. The translation transporter 34 and the rotator 48 are synchronized and arranged with the deflector 14 such that either the entire surface or portions of the surface of the workpiece may be inspected.

For instance, in one embodiment, the translation transporter 34 and the rotator 48 are synchronized and arranged with the deflector 14 so as to form a spiral-shaped narrow angle scan across the surfaces of the workpiece during rotational and translational travel along the material path P. This is illustrated with reference to FIG. 5. This spiral-shaped scan is illustrated in FIG. 5A. The deflector therefore scans the optical beam in a radial direction θ with rotating motion and linear, lateral, or translational motion Y, shown in FIG. 4, to implement a spiral scan pattern.

The direction of the scan path a corresponds to the direction of translational travel Y of the workpiece W. The narrow angle scan begins at the outer radius of the rotating workpiece, and the workpiece is rotated at a predetermined speed. The stage member upon which the workpiece W is mounted moves synchronously with the rotation to create a smooth spiral. As the radius decreases, the rotational speed, as well as the translational speed, are gradually increased to keep the scan rate of the deflector 14 substantially constant. This scan process continues until the innermost five rotations at which a relatively constant rotational speed, i.e., about 200 rpm, is maintained. As such, the surface of the workpiece is substantially scanned. The scan can be started from the center of the workpiece, and translated outward to the outer edge of the workpiece without loss of generality.

It must be understood that although the apparatus and methods of the present invention are illustrated in conjunction with a spiral scan path for inspecting the workpiece, that the present invention should not be limited to this scan path geometry. Specifically, the apparatus and methods of the present invention are contemplated for use with many scan path geometries, including even the most rudimentary of scan paths such as a back and forth incremented scan of the workpiece.

Figure 5:
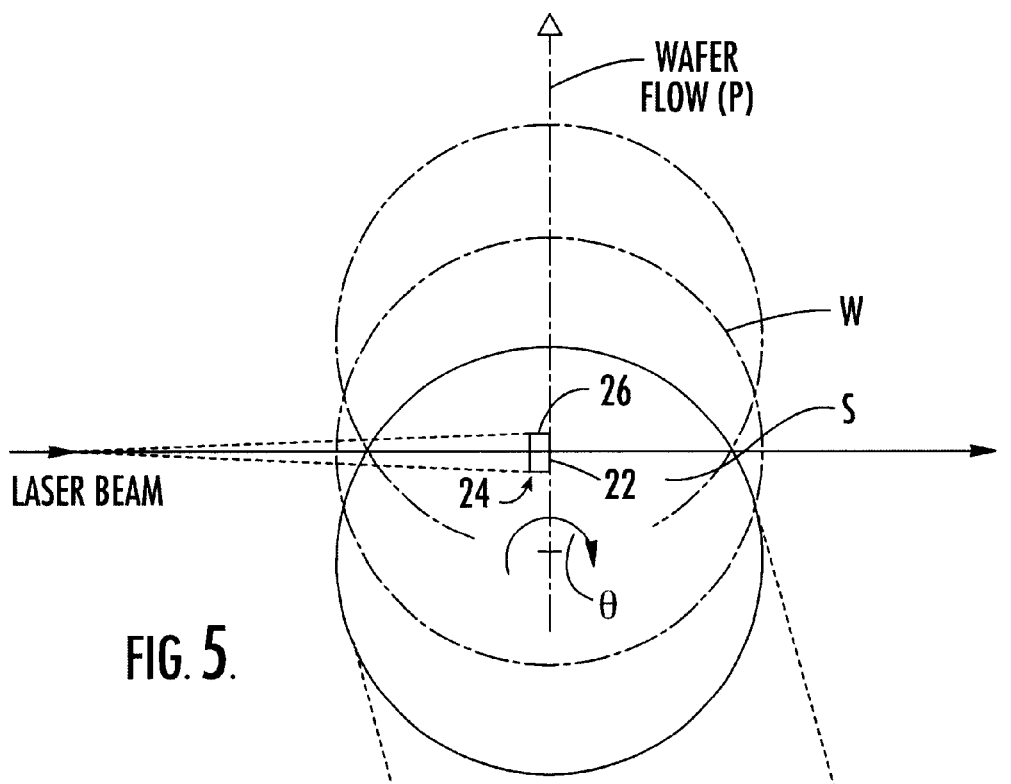
FIGS. 5 and 5A are graphic representations of the scan path used to inspect the surface of a workpiece for defects in a conventional workpiece inspection device.
Figure 5A:
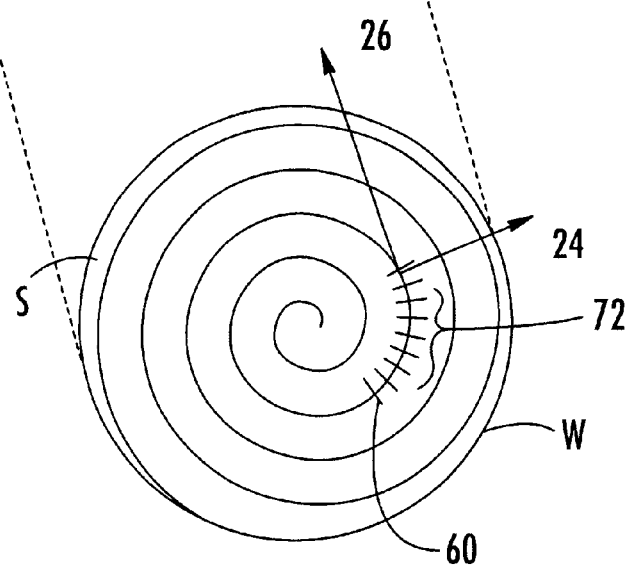

Importantly as also illustrated in FIG. 5, the optical beam via the deflector forms an optical scan region 22 on the surface the workpiece to perform a scan. The scan region is defined by an in-scan dimension 24 that relates to the scan path of the light beam. Specifically, the scan path is the sweep of the optical beam through an angle a controlled by the deflector. Further, the scan region includes a cross-scan dimension 26 that is associated with the width of the beam. In the spiral scan path illustrated in FIGS. 5 and 5A, the in-scan dimension is radial with respect to the center of the workpiece and the cross-scan dimension is tangential to the scan path of the spiral, or perpendicular to the beam sweep deflection.

As discussed above, a limitation on the particle sensitivity of many wafer inspection devices is the shot noise in the dark channel detectors of the wafer inspection device. In light of this, the present invention provides apparatus and methods that filter the optical signals received by the detectors prior to determination as to whether the workpiece includes defects. Specifically, the apparatus and methods of the present invention filter the optical signals received by the optical detectors in a cross-scan direction to reduce the noise in the optical signal. Further, in some embodiments, the apparatus and methods of the present invention filters the optical signals in the in-scan direction also. As such, signal noise, which may overshadow optical signals representing smaller defects in the workpiece, are advantageously eliminated from the optical signal.

Figure 6:
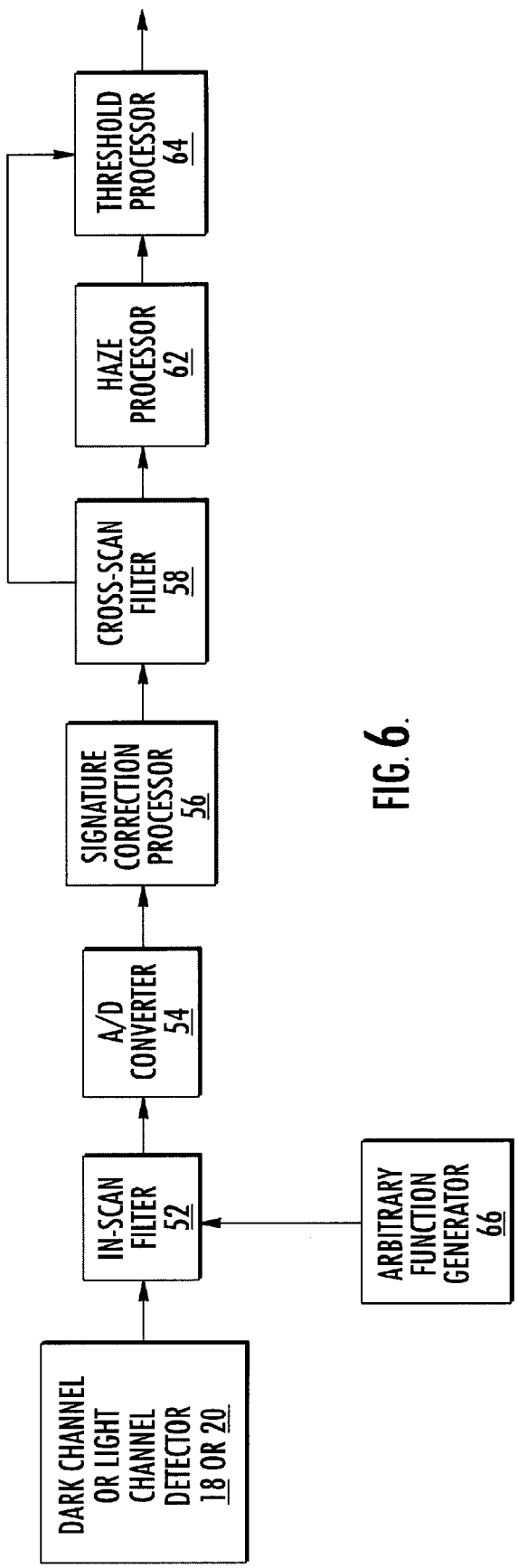
FIG. 6 is a block diagram of an apparatus for detecting defects in the surface of a workpiece according to one embodiment of the present invention.

With reference to FIG. 6, an apparatus for detecting defects in a workpiece according to one embodiment of the present invention is shown. FIG. 6 illustrates some of the components of the signal processor 28, shown in FIG. 1. As illustrated, the apparatus of the present invention may be used with either the light or dark channel signals from either the dark or light channel detectors, 18 and 20, respectively. Connected to either the dark or light channels is an analog-to-digital (A/D) converter 54 and a cross-scan filter 58 for filtering noise in the signal that is present in the cross-scan dimension 26 of the scan region 22, shown in FIG. 5.

In the embodiment illustrated, the cross-scan filter is a digital filter, and as such, the A/D converter is used to digitize the signal prior to filtering. However, it must be understood that the cross-scan filter described below may be implemented as either a digital or analog filter and should not be limited to either form.

Figure 7:
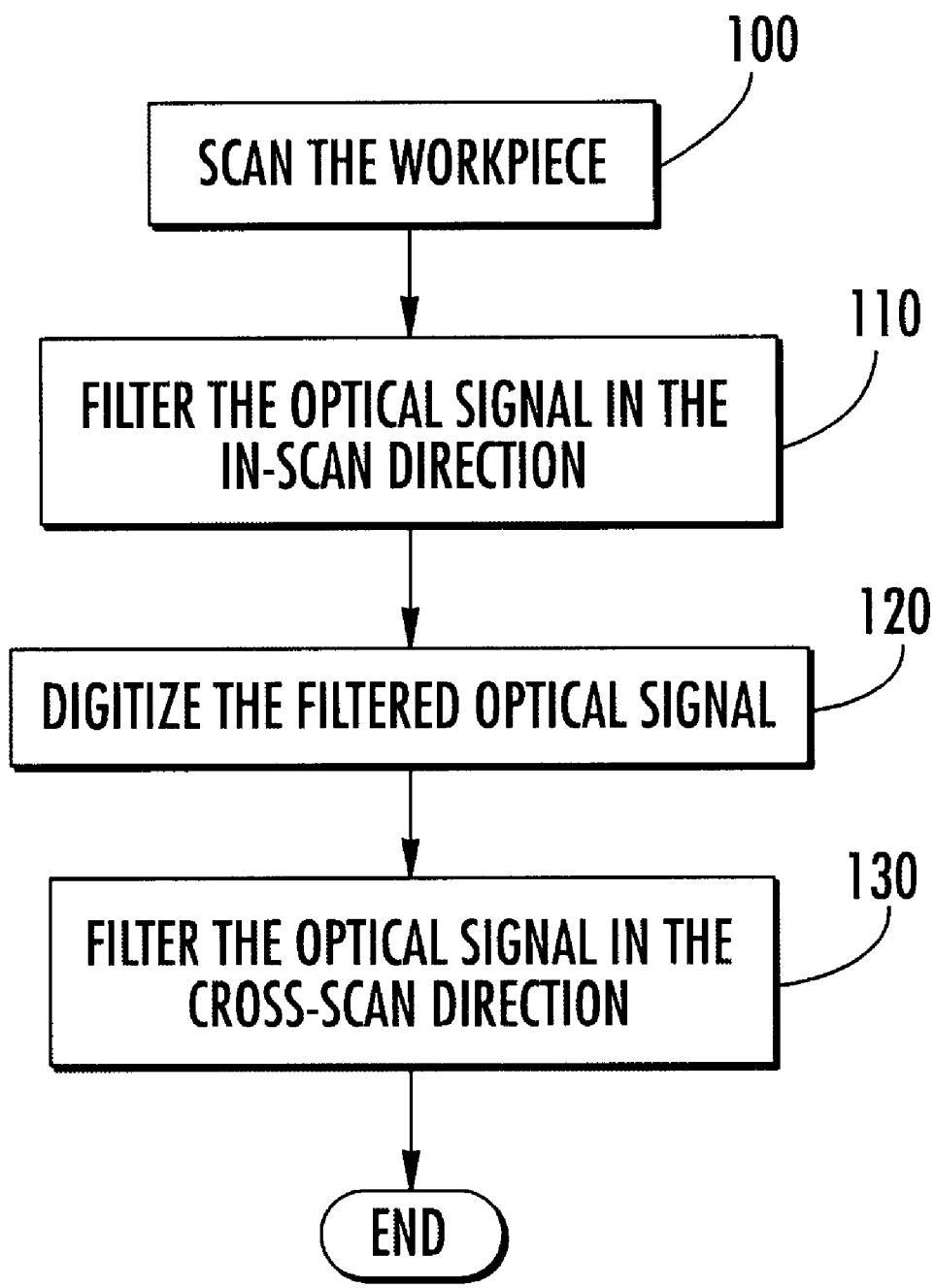
FIG. 7 is a block diagram of the operations performed to detect defects in the surface of a workpiece according to one embodiment of the present invention.

With reference to FIGS. 5, 5A, and 7, in operation, the deflector in conjunction of the translation transporter and rotator, scans the workpiece along a scan path θ. (See step 100). At each position, the deflector dithers the optical beam to perform a sweep 60, (see FIG. 5A), through an angle α on the workpiece. This sweep 60 represents one scan. Further, the distance between each scan, caused by the movement and rotation of the workpiece between sweeps, is typically referred to as the tangential scan pitch. The tangential scan pitch is a tangential distance between scans with respect to the path of the workpiece.

For each scan, the A/D converter initially converts the filtered optical signal received by either the dark or light channel detectors into a digital signal having data points representing a scan or sweep 60 by the optical beam B in the scan region 22. (See step 120). The digital signal is then provided to the cross-scan filter where the signal is filtered in the cross-scan dimension to remove signal noise. (See step 130).

The operation of the cross-scan filter is more specifically illustrated with reference to FIGS. 5, 5A, 8, and 9. Specifically, with reference to FIG. 5, the cross-scan filter filters signal noise present in the cross-scan dimension 26 of the scan zone 22. To filter the noise in the cross-scan dimension, the cross-scan filter effectively averages the values of several sequential scans together in an optimal manner to reduce the effects of noise in the cross-scan dimension of the optical signal. Specifically, as shown in FIG. 5A, the light source and deflector, in conjunction with the translational transponder and rotator performs several scans 72 along the path θ of the scan. Each of these scans defines a scan region having an in-scan dimension 24 and a cross-scan dimension 26. As mentioned previously, the in-scan dimension is in the direction of the scan and is in a radial direction with respect to the center of the workpiece. Further, the cross-scan dimension is in a direction that is tangential to the spiral path with which the workpiece is scanned.

Figure 8:
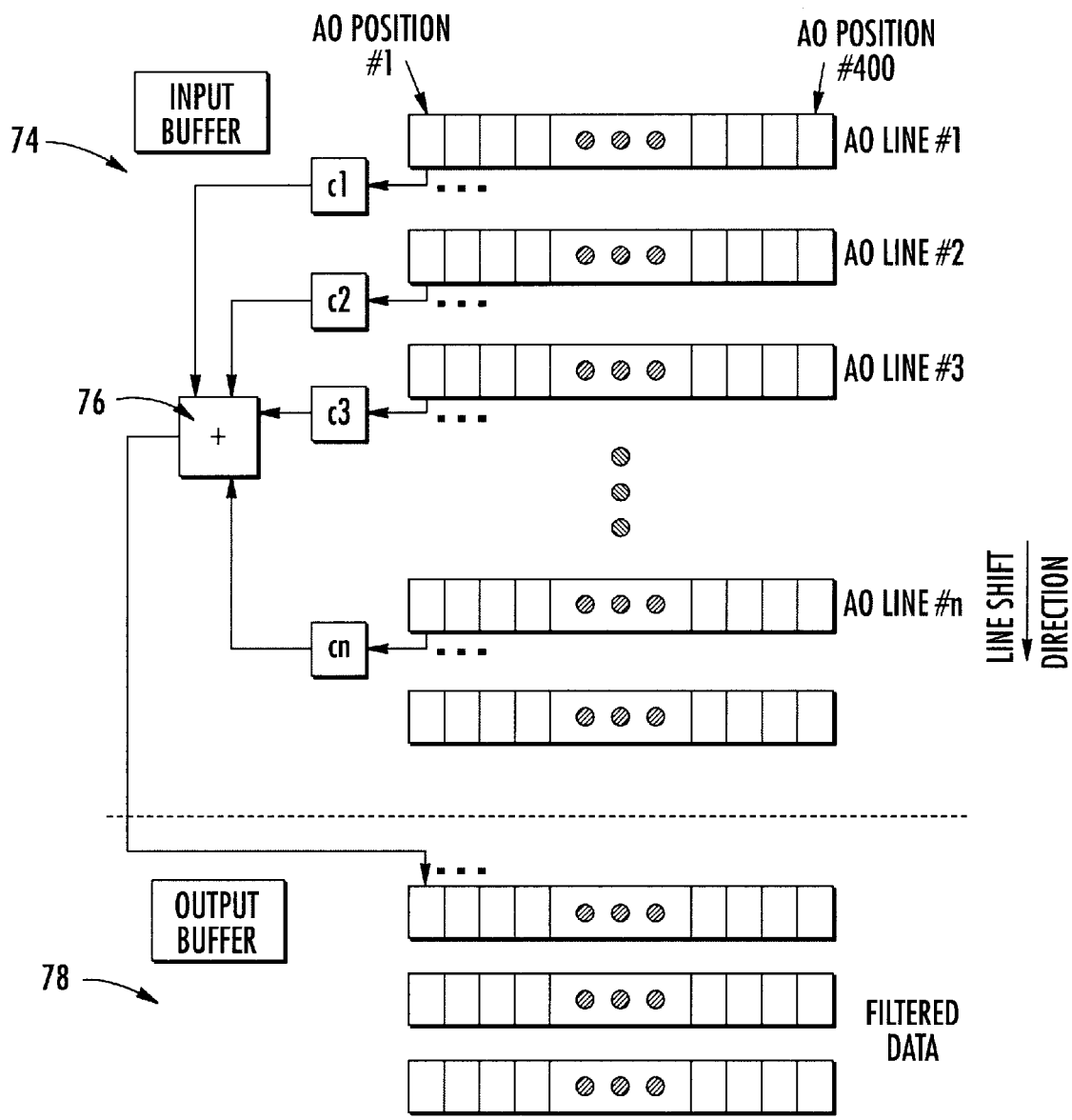
FIG. 8 is an operation block diagram of an apparatus for filtering an optical signal received by an inspection device in a cross-scan direction according to one embodiment of the present invention.
Figure 9:
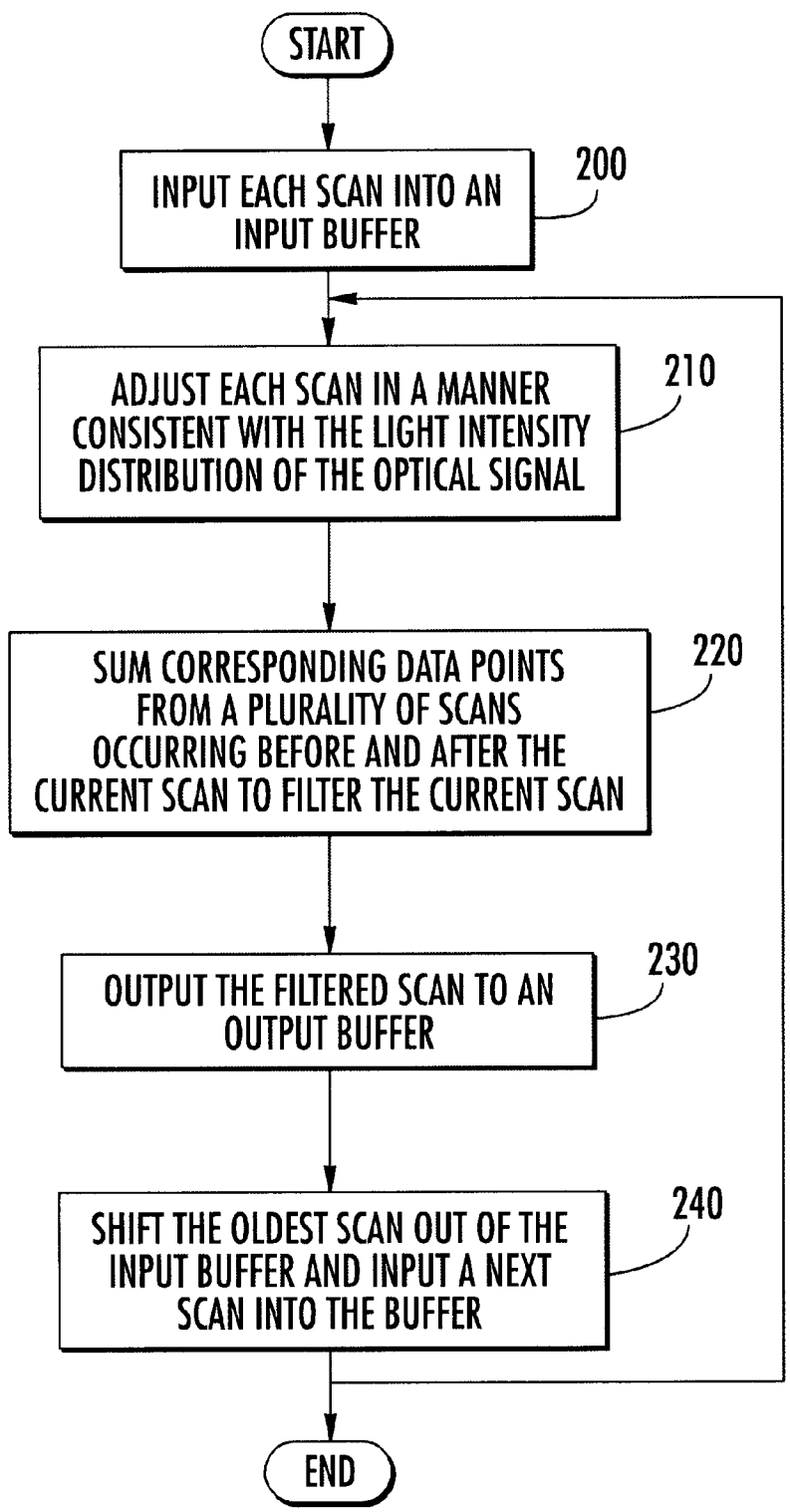
FIG. 9 is a block diagram of the operations performed to filter an optical signal received by an inspection device in a cross-scan direction according to one embodiment of the present invention.

With reference to FIGS. 8 and 9, for each scan, the A/D digitizes each scan into digital signals. Each digitized scan signal is then provided to an input buffer 74 of the cross-scan filter 58. (See step 200). Each scan is stacked in the buffer as scan lines, designated as AO line #1–#n, and each scan line includes a set number of data points, such as 400 data points, digitally representing the optical signal from the scan. To cross-scan filter each scan in the buffer, the cross-scan filter, using a windowing technique, sums corresponding data points in a plurality of scans occurring before and after the present scan together with a summer 76. (See step 220). The processor then outputs the filtered scan to an output buffer 78 for use in determining whether the workpiece includes defects. (See step 230).

Importantly, summing the individual data points of a plurality of scans occurring sequentially before and after the present scan reduces the noise in the scan. Specifically, because shot noise exhibits Poisson noise statistics, by adding the data points (weighted by multiplier coefficients) of several scans, the cross-scan filter of the present invention can effectively reduce the noise content in each scan of the optical beam.

With reference to FIGS. 8 and 9, as an example of the operation of the cross-scan filter, the cross-scan filter may be designed to use 10 scans occurring before and 10 scans occurring after the present scan in order to cross-scan filter noise from the present scan. Each of these scans would be designated in the buffer as AO lines #1–#21. In this embodiment of the present invention, for each scan, the cross-scan filter sums the individual corresponding digital values of the 10 scans prior to the present scan and the 10 scans subsequent to the present scan, weighted by their corresponding multiplier coefficients, to the individual bits of the present scan using the summer 76. (See step 220). The present filtered scan is then provided to an output buffer 78 as a scan that has been filtered in the cross-scan directions for use in determining whether the workpiece includes defects. (See step 230). These steps are performed for each AO position.

As discussed above, to filter the next scan, the cross-scan filter uses a windowing technique. Specifically, the input buffer includes 10 scans occurring before the present scan and 10 scans occurring after the present scan. When the present scan is filtered, the oldest of the 10 scans occurring prior to the present scan is shifted out of the input buffer and new scan is added to the top of the buffer. (See step 240). The steps are then repeated for the next scan using the 10 scans occurring prior to the scan and 10 scans occurring after the scan. As such, each scan is filtered with a predetermined number of scans occurring sequentially before and after the scan to provide a filtered signal.

As discussed above, the wafer inspection system uses an optical beam to scan the workpiece for defects. As known in the art, many light sources output optical beams that have a non-uniform light intensity distribution. For example, many light sources output optical beams that have a Gaussian light intensity distribution across the optical beam. In other words, the optical beam tends to have a higher intensity of light at the center of the beam than on the edges of the beam. In this instance, it may be advantageous to configure the cross-scan filter such that it matches the light intensity distribution of the optical beam generated by the light source to thereby properly filter the optical signal.

For example, in one embodiment of the present invention, the light source generates an optical beam having a Gaussian light intensity distribution. In this embodiment, since the spot of the optical beam is Gaussian, a Gaussian pulse shape is produced as the optical beam sweeps across a defect in the workpiece and is detected by the optical detector. To properly filter the optical signal in the cross-scan direction, the cross-scan filter should have a Gaussian filter characteristic that substantially matches the Gaussian light intensity distribution of the signal, such that the cross-scan filter filters the different portions of the signal accordingly.

To match the cross-scan filter to the Gaussian light intensity distribution of the optical beam, the cross-scan filter, according to one embodiment of the present invention, uses cross-scan coefficients, ($c_1 \ldots c_n$), to properly weight each of the plurality of scans used to filter the present scan. (See step 210). Specifically, prior to adding the individual corresponding data points of each scan occurring prior to and after the present scan to filter the scan, (see step 220), the processor first multiplies each scan by a different cross-scan coefficient $c_n$, where each cross-scan coefficient value is chosen, such that when the scans are added together, the plurality of scans are weighted accordingly to correspond to the Gaussian light intensity distribution of the optical beam. In other words, the cross-scan coefficients are such that the present scan is multiplied by the largest coefficient value, and the remaining scans surrounding the present scan used for filtering the present scan are multiplied by lower cross-scan coefficients with those scans further removed from the present scan being multiplied by ever smaller cross-scan coefficients, thereby representing the Gaussian light intensity distribution of the optical beam in the cross-scan direction. (See step 210).

Figure 10:
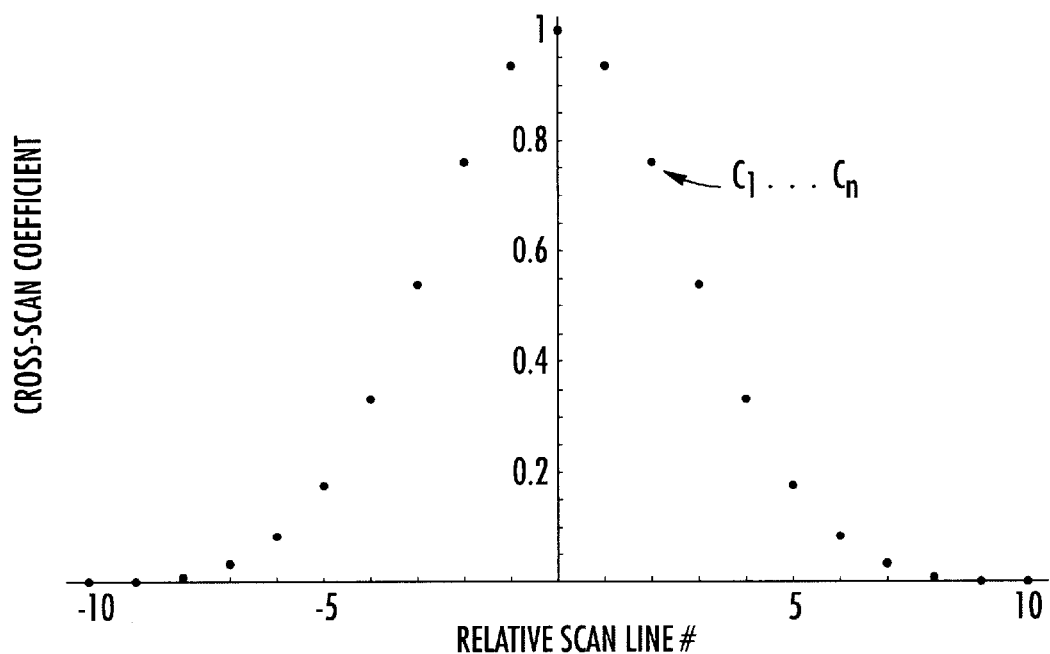
FIG. 10 is a graphic representation of the cross-scan coefficient values used in one embodiment of the present invention to compensate for the light intensity distribution of the optical beam used to inspect a workpiece.

FIG. 10 provides a graphic representation of the cross-scan coefficients used in the cross-scan filter according to one embodiment of the present invention. As can be seen from this graph, the cross-scan coefficient values are chosen to represent a Gaussian distribution across the plurality of scans occurring sequentially prior to and after the present scan and used for filtering the present scan. The formula for computing these cross-scan coefficients according to one embodiment of the present is based on the cross-scan dimension 26 of the optical beam, as shown in FIG. 5, the angle β that the optical beam makes with respect to the surface of the workpiece, and the distance between each of the scans. The distance between each scan is typically referred to as tangential scan pitch and is a tangential distance between scans with respect to the path θ of the scan.

The formula is shown below:

$$e^{\left(\frac{-2y^2}{\left(\frac{wy}{\cos\beta}\right)^2}\right)}$$

where wy=the laser spot radius at $1/e^2$ power level in the cross-scan direction, i.e., the cross-scan dimension 26;

β is the that the beam B makes with respect to the surface of the workpiece; and y=(number of scans) X (tangential scan pitch), where number of scans is an integer from −n to n. In this formula, n should be chosen such that $c_n < 0.05$.

It may be noted that the cross-scan coefficients illustrated in FIG. 10 according to one embodiment of the present invention are symmetrical. This symmetry can be used to reduce the number of multiplies required to determine the cross-scan coefficients. Specifically, the above formula may be rewritten as:

$$y = \sum_{i=-n}^{n} c_i x_i = x_0 + \sum_{i=1}^{n} c_i (x_i + x_{-i})$$

where $x_i$ are the data values in the cross scan direction for a given output value, y, for a given in-scan data position. This reduction of multiply operations can minimize the amount of computational hardware required in signal processor 28.

As described above, the apparatus and methods of the present invention filter the optical signal reflected from the workpiece in a cross-scan direction to reduce shot noise in the detected signal and increase the sensitivity of the inspection device. In addition to filtering the optical signal in the cross-scan direction, in some embodiments, it is advantageous to also filter the optical signal in the in-scan direction. For this reason, with reference to FIG. 8, in one embodiment, the apparatus of the present invention further includes an in-scan filter 52 sometimes referred to as a front end circuit for filtering noise in the optical signal reflected either as a scatter or specularly from the workpiece. Importantly, with reference to FIGS. 5 and 5A, the in-scan filter is used to filter optical noise in the signal appearing in a direction 24 parallel to the scan of the optical beam through the scan path α, and in the case of the present embodiment, radially with respect to the center of the workpiece.

As with the cross-scan filter, the in-scan filter is typically configured such that it matches the light intensity distribution of the optical beam generated by the light source to thereby optimally filter the optical signal. For example, in one embodiment of the present invention, the light source generates an optical beam having a Gaussian light intensity distribution. In this embodiment, since the spot of the optical beam is Gaussian, a Gaussian pulse shape is produced as the optical beam sweeps across a defect in the workpiece and is detected by the optical detector. To optimally filter the optical signal in the in-scan direction in a least squares sense, the in-scan filter should have a Gaussian pulse response that substantially matches the Gaussian light intensity distribution of the signal, such that the in-scan filter filters the different portions of the signal accordingly. For example, in one embodiment of the present invention, the in-scan filter has modifiable analog tapped-delay line filter coefficients that substantially match the Gaussian light intensity distribution of the optical beam in the in-scan direction.

An in-scan filter having modifiable tapped-delay filter coefficients is commercially available from Data Delay Devices, Inc., Clifton, N.J., such as the DDU4C.

Figure 2:
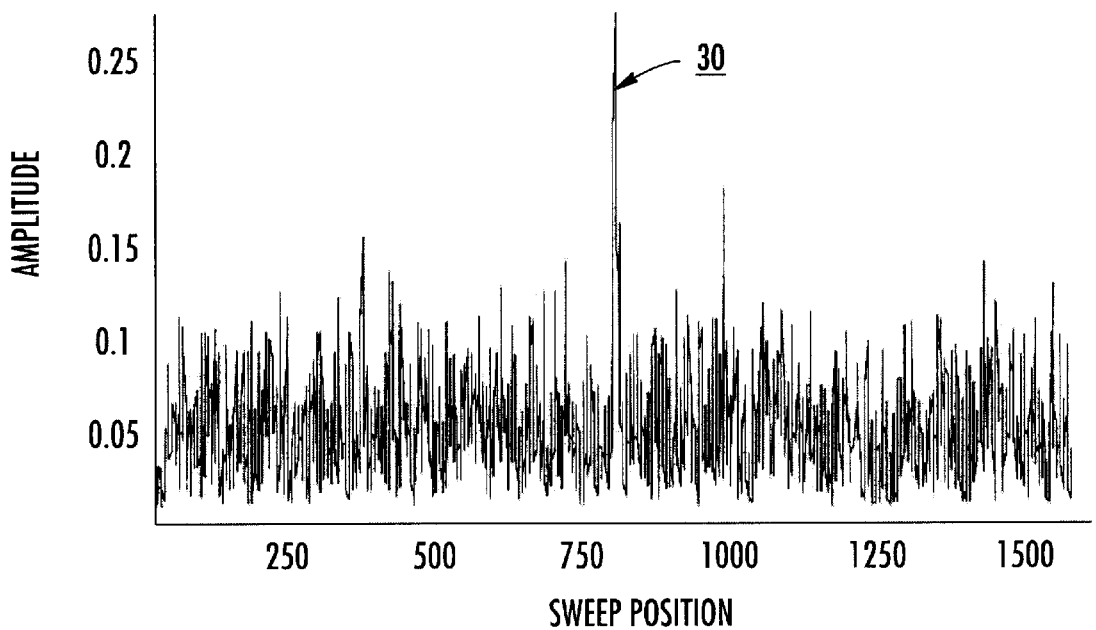
FIG. 2 is a graphic representation of an optical signal received by a workpiece inspection device during inspection of the surface of a workpiece.

With reference to FIG. 7, in operation, the in-scan filter initially receives an optical signal from either the light or dark channel detector similar to the optical signal illustrated in FIG. 2. (See step 100). The in-scan filter filters the signal in the in-scan direction and reduces the shot noise to produce a filter signal similar to the signal in FIG. 3. (See step 110). This filtered signal is then provided to the A/D converter and the cross-scan filter for cross-scan filtering, as described previously.

Figure 3:
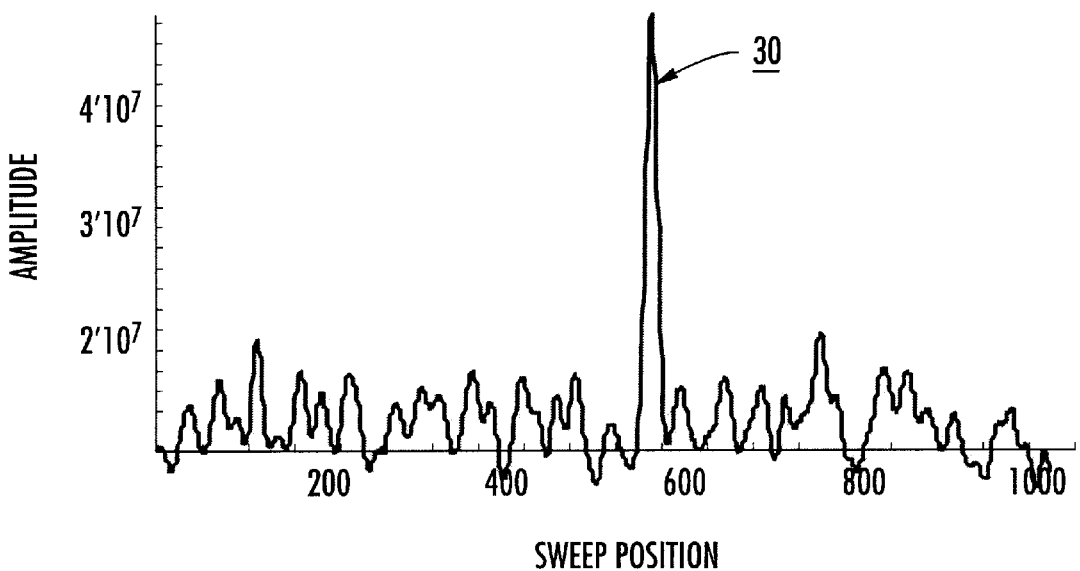
FIG. 3 is a graphic representation of an optical signal receive by a workpiece inspection device during inspection of the surface of a workpiece that has been filtered in the in-scan direction.
Figure 11:
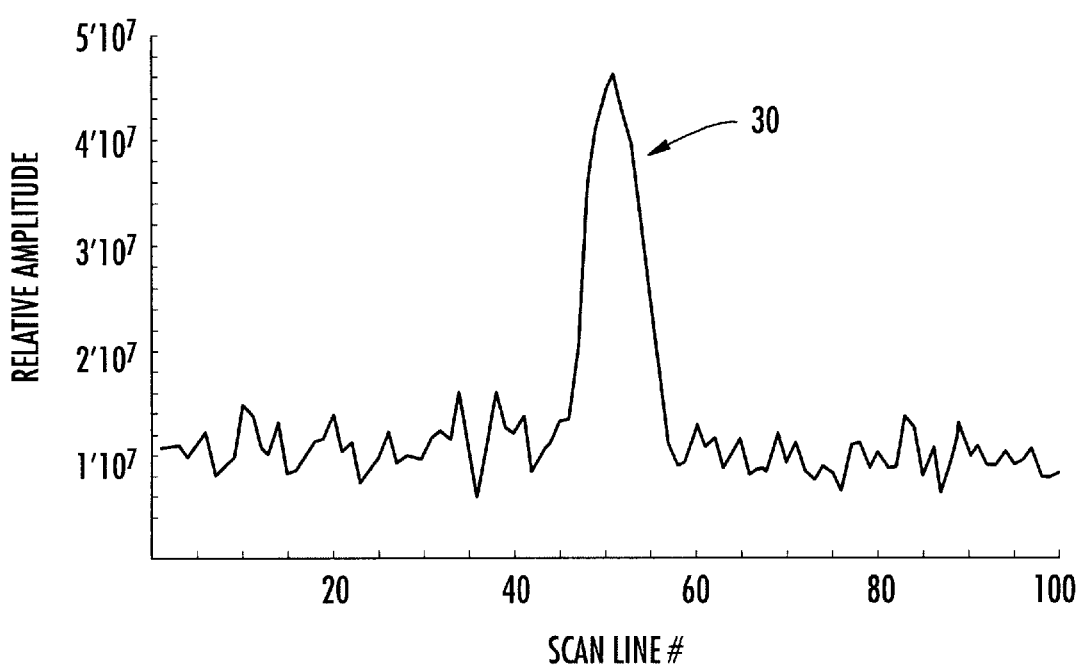
FIG. 11 is a graphic representation of an optical signal receive by a workpiece inspection device during inspection of the surface of a workpiece that has been filtered in the in-scan direction and digitized according to one embodiment of the present invention.

As discussed, in this embodiment of the present invention, the apparatus filters the optical signals reflected from the workpiece in both an in-scan and cross-scan direction to thereby reduce the noise in the optical signal and increase the sensitivity of the wafer inspection system. This increased sensitivity can be seen graphically from FIGS. 2, 3, 11, and 12. Specifically, the in-scan filter of the present invention filters the optical signal of FIG. 2 and generates a filtered optical signal that has been filtered in the in-scan direction, as shown in FIG. 3. As described above, the cross-scan filter filters this signal in the cross-scan direction, thereby further reducing the noise in the signal. Specifically, FIG. 11 illustrates the optical signal for one AO position as a function of the scan row number after the data was filtered by the in-scan filter and digitized by the A/D converter. As illustrated in FIG. 11, this signal still contains a significant shot noise component.

Figure 12:
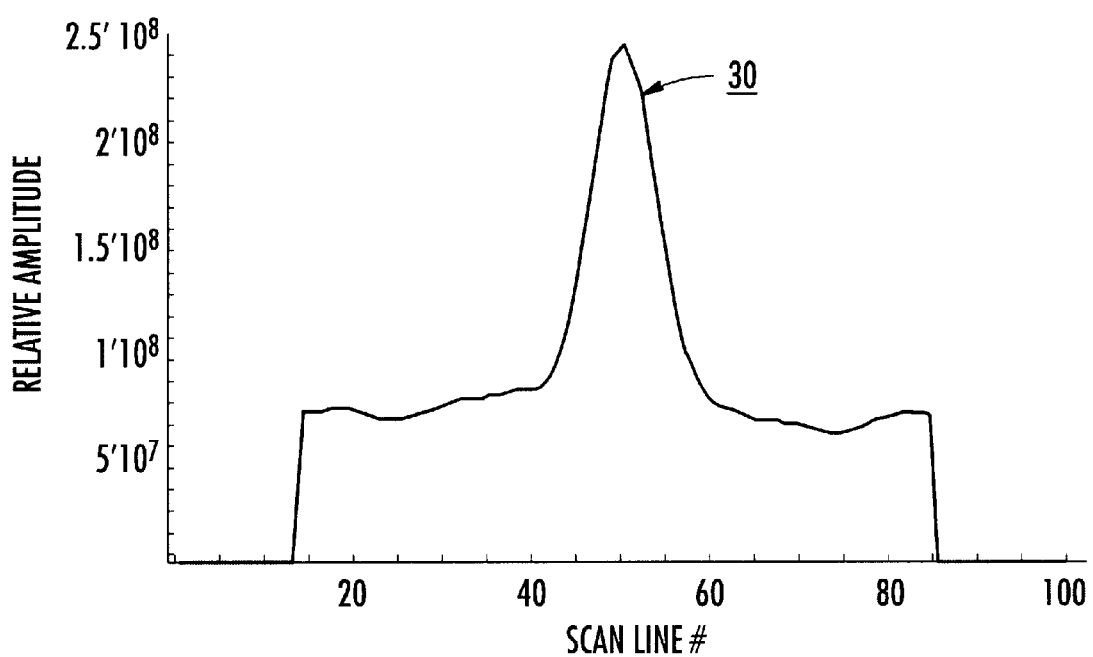
FIG. 12 is a graphic representation of an optical signal receive by a workpiece inspection device during inspection of the surface of a workpiece that has been filtered in the in-scan direction, digitized, and filtered in the cross-scan direction according to one embodiment of the present invention.
Figure 13:
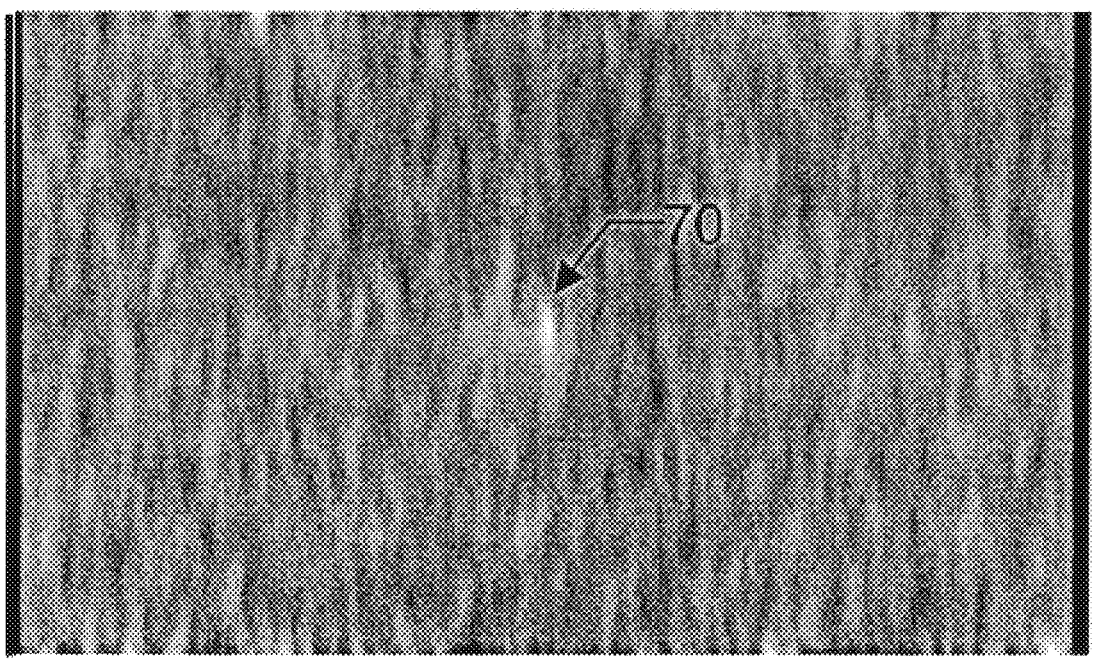
FIG. 13 is a visual representation of defects in a workpiece as detected and displayed by an inspection device after the optical signal has been filtered in both the in-scan and cross-scan directions according to one embodiment of the present invention.

However, FIG. 12 illustrates the optical signal after it has been filtered by the cross-scan filter. As shown, the optical signal, as filtered by both the in-scan and cross-scan filters, has a substantially reduced noise level. Further, the peak 30 indicating the defect is much more pronounced. This reduction in noise can also be seen in the visual image provided by the inspection device. FIG. 13 illustrates an image from the scan of a workpiece. The image shows a defect 70 in the workpiece as detected by the apparatus and method of the present invention.

As illustrated, the addition of the cross-scan filter increases the sensitivity of the wafer inspection device. Provided below is a table illustrating the sensitivity improvement of wafer inspection device according the present invention with and without cross scan filtering as a function of the tangential scan pitch:

| Tangential Scan Pitch | Sensitivity w/o Cross Scan | Sensitivity w/ Cross Scan |
|---|---|---|
| 24 microns | 75 nm | 71 nm |
| 12 microns | 71 nm | 64 nm |
| 7 microns | 69 nm | 59 nm |

As can be seen from this table, the use of cross-scan filtering increases the sensitivity of the wafer inspection system, such that the system can reliably detect smaller defects in the workpiece.

Another important factor of the apparatus and methods of the present invention that is illustrated in the table is that the sensitivity is improved when the scan pitch is reduced, and the throughput is decreased. For example, for the 7 micron case, the particle diameter that can be sensed is 1.17 times smaller. This is significant as it represents an effective increase in the signal to noise ratio of 2.6 times, (since the signal to noise ratio is a function of PSL diameter to the sixth power). This increased sensitivity makes it possible to meet the SEMI specifications at a 12 micron scan pitch.

In addition to providing an in-scan and cross-scan filter for filtering the optical signal reflected by the workpiece, in one embodiment, the apparatus and method of the present invention may further include a signature correction processor 56 that compensates for consistent, repetitive variations in the intensity of the optical signal emitted by the light source. Specifically, these variations can be caused by variations in the transmission efficiency of the deflector as a function of the scan angle. These variations may be of a magnitude such that they affect the inspection sensitivity of the workpiece. In this instance, the signature processor 56 may adjust the optical signal received by the optical detectors for these known variations in the optical signal. The signature processor typically adjusts the optical signal prior to the signal being cross-scan filtered.

For instance, in one embodiment, a predetermined compensation factor representing weighted data points may be stored in the signature processor representing the known historical variations in the light source. In this instance, the signature processor would subtract the individual data points of the predetermined compensation factor from the digitized individual data points of the optical signal to compensate the optical signal. In another embodiment, the signature processor may generate a compensation factor by averaging several scans of the workpiece together and determining which portions of the signal have constant values over several scans, thereby representing known inconsistencies in the optical beam.

As discussed above, the apparatus and method of the present invention filter the optical signal reflected from the workpiece in both the in-scan and cross-scan directions prior to analyzing the optical signal to determine if defects exist in the workpiece. In one embodiment of the present invention, the apparatus of the present invention further includes a haze processor 62 and a threshold processor 64 for determining whether the workpiece has defects.

The haze processor is used to calculate a background reference signal that is based on the background scatter from the workpiece surface. This background scatter may be present due to several factors. For example, one source of the background scatter is the roughness of the surface of the workpiece. Although the surface of the workpiece is typically polished during manufacture, the surface will still have a level of roughness that is detected in the optical detectors. The haze processor of the present invention typically uses a windowing technique across the surface of the workpiece to identify noise or haze introduced into the optical signal due to irregularities in the workpiece, such as areas of surface roughness.

For example, in one embodiment of the present invention, haze processor includes a buffer having a plurality of scans occurring previous to and after the present scan. The buffer selects a predetermined number of digitized points from each scan and computes an average based on these points. This average is sometimes referred to as a gray level. For each scan, as it is being processed to determine whether it indicates that the workpiece includes errors and typically following in-scan and cross-scan filtering, the haze processor subtracts the gray level from the data points of the scan.

To determine whether the scan indicates that the workpiece has a defect, the threshold processor analyzes the data points of the scan that have positive values when subtracted from the gray level determined by the haze processor. If the scan includes data points that are greater than or equal to the threshold value, the data value is retained for further processing and defect characterization. The data points in the scan that correspond to the defect are stored for later comparison to a coordinate position map of the workpiece for displaying to the user where the defects are located on the workpiece.

With reference to FIG. 6, the apparatus and methods of the present invention may include an in-scan and cross-scan filter, an AMD converter, a signature processor, haze processor, and threshold processor for detecting defects in a workpiece. It must be understood, however, that not all of these components are needed for every embodiment. Specifically, in one embodiment of the present invention, the apparatus may include only an A/D converter, cross-scan detector, and threshold processor for detecting defects in a workpiece. While in other embodiments, the apparatus may further include an in-scan filter.

In addition to the various filters and processors used to determine whether a workpiece has defects, the apparatus of the present inventions according to one embodiment, may also include an arbitrary function generator 66 for testing the inspection system. Specifically, the arbitrary function generator may include a buffer containing a simulating a stream of data for testing the inspection device. The stream of data may simulate defects in a workpiece, noise, and/or calibrated ramp signals. This stream of data may be applied in place of the optical signal regularly received by the optical detectors, and the result of the simulated stream may be analyzed to determine whether the inspection system is operating correctly.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for scanning a workpiece for defects, said apparatus comprising:

a light source for illuminating the workpiece with an optical beam having in-scan and cross-scan dimensions, said light source adapted to sequentially illuminate each of a plurality of different portions of the workpiece in a predetermined scan direction to thereby define a plurality of scans, wherein the in-scan dimension of the optical beam extends parallel to the predetermined scan direction and the cross-scan dimension of the optical beam extends perpendicular to the predetermined scan direction, and wherein said light source emits an optical beam having a predetermined light intensity distribution in the cross-scan dimension and illuminates different positions of the workpiece in a respective scan with light having different intensities;

a receiver for receiving optical signals reflected from the workpiece during each of the plurality of scans; and a cross-scan filter for receiving a data set corresponding to the optical signals received by said receiver during a respective scan, said cross-scan filter adapted to filter the data set of the respective scan in the cross-scan dimension of the optical beam, wherein said cross-scan filter generates an adjusted data set for the respective scan that accounts for the predetermined light intensity distribution of the optical beam in the cross-scan dimension of the optical beam by multiplying the individual data points of the data set by a predefined cross-scan coefficient that accounts for the differences in the magnitude of light that illuminates the different positions of the workpiece in the cross-scan dimension.

2. An apparatus according to claim 1, wherein said cross-scan filter, for each respective scan of said light source, receives a data set having individual data points representing the optical beam reflected from the workpiece at different respective positions along the scan direction of the light source, and wherein said cross-scan filter individually filters each data point of the respective scan based upon a corresponding data point of a data set representing the optical signals received by said receiver during another scan to thereby filter the data set of the respective scan in the cross-scan dimension of the optical beam.

3. An apparatus according to claim 2, wherein said cross-scan filter individually adds each data point of the adjusted data set of the respective scan to a corresponding data point of an adjusted data set corresponding to an optical signal received by said receiver during another scan that has been adjusted by another predefined cross-scan coefficient to thereby filter the adjusted data set in the cross-scan dimension of the optical beam.

4. An apparatus according to claim 2, wherein said light source emits an optical beam having a predetermined Gaussian light intensity distribution, such that said light source illuminates portions of the workpiece located in a middle portion of a scan with light having greater intensity than portions of the workpiece located on opposed end portions of the scan.

5. An apparatus according to claim 4, wherein said cross-scan filter generates an adjusted data set for the respective scan that accounts for the predetermined Gaussian light intensity distribution of the optical beam, wherein said cross-scan filter generates the adjusted data set by multiplying the individual data points of the data set by a predefined cross-scan coefficient that account for the differences in the magnitude of light that illuminates the different positions of the workpiece in the cross-scan dimension.

6. An apparatus according to claim 5, wherein said cross-scan filter filters the data set of the respective scan in the cross-scan dimension of the optical beam based on a plurality of data sets corresponding to scans of the workpiece occurring prior to and after the respective scan, wherein said cross-scan filter generates adjusted data sets for each of the plurality of data sets to account for the predetermined Gaussian light intensity distribution of the optical beam by multiplying the individual data points of each data set by a respective predefined cross-scan coefficient, wherein said cross-scan filter multiplies the individual data points of the data sets corresponding to scans occurring closer in time to the respective scan with greater cross-scan coefficient values than the individual data points of the data sets corresponding to scans occurring further in time from the respective scan, and wherein said cross-scan filter filters the adjusted data set of the respective scan in the cross-scan dimension of the optical beam by adding the corresponding individual data points of the plurality of adjusted data sets corresponding to scans of the workpiece occurring prior to and after the respective scan to the individual data points of the adjusted data set of the respective scan.

7. An apparatus according to claim 2 further comprising an in-scan filter for filtering the optical signals received by said receiver during a respective scan, said in-scan filter adapted to filter the optical signals in the in-scan dimension of the optical beam.

8. An apparatus according to claim 7, wherein said in-scan filter filters the optical signals based on the predetermined light intensity distribution of the optical beam in the in-scan dimension, and wherein said in-scan filter has a spectral frequency characteristic corresponding to a spectral characteristic of the predetermined light intensity distribution of the optical beam.

9. An apparatus according to claim 8, wherein said light source emits an optical beam having a predetermined Gaussian light intensity distribution, such that said light source illuminates portions of the workpiece located in a middle portion of a scan with light having greater intensity than portions of the workpiece located on opposed end portions of the scan, wherein said in-scan filter has a Gaussian frequency spectral characteristic that corresponds to the predetermined Gaussian light intensity distribution of the optical beam, and wherein said in-scan filter filters the optical signals based on the predetermined Gaussian light intensity distribution of the optical beam.

10. An apparatus according to claim 1 further comprising a processor for removing optical noise in a scan caused by irregularities in a surface of the workpiece, wherein, for each respective scan of said light source, said processor receives a data set having individual data points representing the optical beam reflected from the workpiece at different positions along the scan direction of the light source, wherein said processor selects a predetermined number of data points from each of a plurality of respective scans of said light source and generates an average scan having individual data points representing the average optical beam reflected from the workpiece at different positions along the scan direction of the light source for the plurality of scans, and wherein said processor subtracts the individual data points of the average scan from the respective individual data bit of each data set for each of the plurality of scans, thereby correcting each data set for irregularities in the surface of the workpiece.

11. An apparatus according to claim 1 further comprising a processor for determining whether the workpiece contains a defect, wherein, for each respective scan of said light source, said processor receives a data set having individual data points representing the optical beam reflected from the workpiece at different positions along the scan direction of the light source, wherein said processor compares each data point of the scan to a threshold value, and wherein said processor identifies portions of the workpiece that have corresponding data points in the scan that are at least as great as the threshold value as potential defects in the workpiece.

12. An apparatus according to claim 1 further comprising a processor for compensating for consistent variations in the intensity of the optical signal emitted by said light source, wherein, for each respective scan of said light source, said processor receives a data set having individual data points representing the optical beam reflected from the workpiece at different positions along the scan direction of the light source, and wherein said processor subtracts from the data set a signature data set having individual data points representing the consistent variations in the intensity of the optical signal emitted by said light source.

13. A method for scanning a workpiece for defects, the method comprising:
illuminating the workpiece with an optical beam having in-scan and cross-scan dimensions, said illuminating comprising sequentially illuminating each of a plurality of different portions of the workpiece in a predetermined scan direction to thereby define a plurality of scans, wherein the in-scan dimension of the optical beam extends parallel to the predetermined scan direction and the cross-scan dimension of The optical beam extends perpendicular to the predetermined scan direction, and wherein the optical beam has a predetermined light intensity distribution in the cross-scan dimension and illuminates different positions of the workpiece in a respective scan with light having different intensities, receiving optical signals reflected from the workpiece during each of the plurality of scans;

constructing a data set corresponding to the optical signals received during a respective scan; and filtering the data set in the cross-scan dimension of the optical beam, wherein said filtering comprises multiplying the individual data points of a data set by a predefined cross-scan coefficient that accounts for the differences in the magnitude or light that illuminates the different positions of the workpiece in the cross-scan dimension.

14. A method according to claim 13, wherein said constructing comprises constructing a data set for each respective scan that has individual data points representing the optical beam reflected from the workpiece at different respective positions along the scan direction, and wherein said filtering comprises individually adjusting each data point of the scan based upon a corresponding data point of a data set representing the optical signals received during another scan to thereby filter the data set in the cross-scan dimension of the optical beam.

15. A method according to claim 14, wherein said individual adjustment comprises individually adding each data point of the adjusted data set of the respective scan to a corresponding data point of an adjusted data set corresponding to an optical signal received during another scan that has been adjusted by another predefined cross-scan coefficient to thereby filter the adjusted data set in the cross-scan dimension of the optical beam.

16. A method according to claim 14, wherein said illuminating comprises illuminating the workpiece with an optical beam having a predetermined Gaussian light intensity distribution, such that portions of the workpiece located in a middle portion of a scan are illuminated with light having greater intensity than portions of the workpiece located on opposed end portions of the scan.

17. A method according to claim 16, wherein said filtering comprises generating an adjusted data set for the respective scan that accounts for the predetermined Gaussian light intensity distribution of the optical beam, wherein said generating comprises multiplying the individual data points of the data set by a predefined cross-scan coefficient that account for the differences in the magnitude of light that illuminates the different positions of the workpiece in the cross-scan dimension.

18. A method according to claim 17, wherein said filtering comprises filtering the data set of the respective scan in the cross-scan dimension of the optical beam based on a plurality of data sets corresponding to scans of the workpiece occurring prior to and after the respective scan, wherein said generating comprises multiplying the individual data points of each data set by a respective predefined cross-scan coefficient, said multiplying comprising multiplying the individual data points of the data sets corresponding to scans occurring closer in time to the respective scan with greater cross-scan coefficient values than the individual data points of the data sets corresponding to scans occurring further in time from the respective scan, and wherein said individual adjustment comprises adding the corresponding individual data points of the plurality of adjusted data sets corresponding to scans of the workpiece occurring prior to and after the respective scan to the individual data points of the adjusted data set of the respective scan.

19. A method according to claim 14 further comprising filtering the optical signals received during a respective scan in the in-scan dimension of the optical beam.

20. A method according to claim 19, wherein said filtering in the in-scan dimension comprises generating an adjusted optical signal that accounts for the predetermined light intensity distribution of the optical beam in the in-scan dimension.

21. A method according to claim 20, wherein said illuminating comprises illuminating the workpiece with an optical beam having a predetermined Gaussian light intensity distribution, such that portions of the workpiece located in a middle portion of a scan are illuminated with light having greater intensity than portions of the workpiece located on opposed end portions of the scan, and wherein said generating comprises generating an adjusted signal for the scan that accounts for the predetermined Gaussian light intensity distribution of the optical beam in the in-scan dimension.

22. A method according to claim 13 further comprising removing optical noise in a scan caused by irregularities in a surface of the workpiece, wherein said removing comprises:

receiving a data set for each respective scan that has individual data points representing the optical beam reflected from the workpiece at different positions along the scan direction;

selecting a predetermined number of data points from each of a plurality of respective scans;

generating an average scan having individual data points representing the average optical beam reflected from the workpiece at different positions along the scan direction for the plurality of scans; and subtracting the individual data points of the average scan from the respective individual data bit of each data set for each of the plurality of scans, thereby correcting each data set for irregularities in the surface of the workpiece.

23. A method according to claim 13 further comprising determining whether the workpiece contains a defect, wherein said determining comprises:

receiving a data set for each respective scan that has individual data points representing the optical beam reflected from the workpiece at different positions along the scan direction;

comparing each data point of the scan to a threshold value; and identifying portions of the workpiece that have corresponding data points in the scan that are at least as great as the threshold value as potential defects in the workpiece.

24. A method according to claim 13 further comprising compensating for consistent variations in the intensity of the optical signal, said compensating comprising:

receiving a data set for each respective scan that has individual data points representing the optical beam reflected from the workpiece at different positions along the scan direction; and subtracting from the data set a signature data set having individual data points representing the consistent variations in the intensity of the optical signal.

25. An apparatus for scanning a workpiece for defects, said apparatus comprising:

a light source for illuminating the workpiece with an optical beam having in-scan and cross-scan dimensions and having a predetermined light intensity distribution in the cross-scan dimension, said light source adapted to sequentially illuminate each of a plurality of different portions of the workpiece in a predetermined scan direction to thereby define a plurality of scans, wherein the in-scan dimension of the optical beam extends parallel to the predetermined scan direction and the cross-scan dimension of the optical beam extends perpendicular to the predetermined scan direction;

a receiver for receiving optical signals reflected from the workpiece during each of the plurality of scans; and a cross-scan filter for filtering a plurality of data sets in the cross-scan dimension, each data set corresponding to the optical signals received by said receiver during a respective scan, each data set also having individual data points representing the optical beam reflected from the workpiece at different respective positions along the scan direction of the light source, wherein said cross-scan filter generates an adjusted data set that accounts for the predetermined light intensity distribution of the optical beam in the cross-scan dimension by multiplying the individual data points of a respective data set by a predefined cross-scan coefficient that accounts for differences in the magnitude of light that illuminates the different positions of the workpiece in the cross-scan dimension, and wherein said cross-scan filter individually adds each data point of the adjusted data set of the respective scan to corresponding data points of a plurality of adjusted data sets that each correspond to an optical signal received by said receiver during another scan and that have been adjusted by another predefined cross-scan coefficient to create a filtered data set that has been filtered in the cross-scan dimension of the optical beam.

26. An apparatus according to claim 25, wherein said cross-scan filter filters the data set of a respective scan in the cross-scan dimension of the optical beam based on a plurality of data sets corresponding to scans of the workpiece occurring prior to and after the respective scan.

27. An apparatus according to claim 26, wherein said cross-scan filter adds individual data points of the data set of the respective scan to corresponding individual data points of the plurality of data sets corresponding to scans of the workpiece occurring prior to and after the respective scan to thereby filter the data set of the respective scan in the cross-scan dimension of the optical beam.

28. An apparatus according to claim 25, wherein said light source emits an optical beam having a predetermined Gaussian light intensity distribution, such that said light source illuminates portions of the workpiece located in a middle portion of a scan with light having greater intensity than portions of the workpiece located on opposed end portions of the scan.

29. An apparatus according to claim 28, wherein said cross-scan filter generates an adjusted data set for the scan that accounts for the predetermined Gaussian light intensity distribution of the optical beam by multiplying the individual data points of the data set by a predefined cross-scan coefficient that accounts for the differences in the magnitude of light that illuminates the different positions of the workpiece in the cross-scan dimension.

30. An apparatus according to claim 29, wherein said cross-scan filter filters the data set of the respective scan in the cross-scan dimension of the optical beam based on a plurality of data sets corresponding to scans of the workpiece occurring prior to and after the respective scan, wherein said cross-scan filter generates adjusted data sets for each of the plurality of data sets to account for the predetermined Gaussian light intensity distribution of the optical beam by multiplying the individual data points of each data set by a respective predefined cross-scan coefficient, wherein said cross-scan filter multiplies the individual data points of the data sets corresponding to scans occurring closer in time to the respective scan with greater cross-scan coefficient values than the individual data points of the data sets corresponding to scans occurring further in time from the respective scan, and wherein said cross-scan filter filters the adjusted data set of the respective scan in the cross-scan dimension of the optical beam by adding the corresponding individual data points of the plurality of adjusted data sets corresponding to scans of the workpiece occurring prior to and after the respective scan to the individual data points of the adjusted data set of the respective scan.

31. An apparatus according to claim 25 further comprising an in-scan filter for filtering the optical signals received by said receiver during a respective scan, said in-scan filter adapted to filter the optical signals in the in-scan dimension of the optical beam.

32. An apparatus according to claim 31, wherein said in-scan filter generates an adjusted optical signal that accounts for the predetermined light intensity distribution of the optical beam in the in-scan dimension, and wherein said in-scan filter has a spectral frequency characteristic corresponding to a spectral characteristic of the predetermined light intensity distribution of the optical beam.

33. An apparatus according to claim 32, wherein said light source emits an optical beam having a predetermined Gaussian light intensity distribution, such that said light source illuminates portions of the workpiece located in a middle portion of a scan with light having greater intensity than portions of the workpiece located on opposed end portions of the scan, wherein said in-scan filter has a Gaussian frequency spectral characteristic that corresponds to the predetermined Gaussian light intensity distribution of the optical beam, and wherein said in-scan filter generates an adjusted signal for the scan that accounts for the predetermined Gaussian light intensity distribution of the optical beam.

34. An apparatus according to claim 25 further comprising a processor for removing optical noise in a scan caused by irregularities in a surface of the workpiece, wherein, for each respective scan of said light source, said processor receives a data set having individual data points representing the optical beam reflected from the workpiece at different positions along the scan direction of the light source, wherein said processor selects a predetermined number of data points from each of a plurality of respective scans of said light source and generates an average scan having individual data points representing the average optical beam reflected from the workpiece at different positions along the scan direction of the light source for the plurality of scans, and wherein said processor subtracts the individual data points of the average scan from the respective individual data bit of each data set for each of the plurality of scans, thereby correcting each data set for irregularities in the surface of the workpiece.

35. An apparatus according to claim 25 further comprising a processor for determining whether the workpiece contains a defect, wherein, for each respective scan of said light source, said processor receives a data set having individual data points representing the optical beam reflected from the workpiece at different positions along the scan direction of the light source, wherein said processor compares each data point of the scan to a threshold value, and wherein said processor identifies portions of the workpiece that have corresponding data points in the scan that are at least as great as the threshold value as potential defects in the workpiece.

36. An apparatus according to claim 25 further comprising a processor for compensating for consistent variations in the intensity of the optical signal emitted by said light source, wherein, for each respective scan of said light source, said processor receives a data set having individual data points representing the optical beam reflected from the workpiece at different positions along the scan direction of the light source, and wherein said processor subtracts from the data set a signature data set having individual data points representing the consistent variations in the intensity of the optical signal emitted by said light source.

37. A method for scanning a workpiece for defects, said method comprising:
   illuminating the workpiece with an optical beam having in-scan and cross-scan dimensions and having a predetermined light intensity distribution in the cross-scan dimension, said illuminating comprising sequentially illuminating each of a plurality of different portions of the workpiece in a predetermined scan direction to thereby define a plurality of scans, wherein the in-scan dimension of the optical beam extends parallel to the predetermined scan direction and the cross-scan dimension of the optical beam extends perpendicular to the predetermined scan direction;
   receiving optical signals reflected from the workpiece during each of the plurality of scans; and
   filtering a plurality of data sets in the cross-scan dimension, each data set corresponding to the optical signals received during a respective scan, each data set also having individual data points representing the optical beam reflected from the workpiece at different respective positions along the scan direction, wherein said filtering comprises generating an adjusted data set that accounts for the predetermined light intensity distribution of the optical beam in the cross-scan dimension, said generating comprising:
      multiplying the individual data points of a respective data set by a predefined cross-scan coefficient that accounts for differences in the magnitude of light that illuminates the different positions of the workpiece in the cross-scan dimension; and
      individually adding each data point of the adjusted data set of the respective scan to corresponding data points of a plurality of adjusted data sets that each correspond to an optical signal received during another scan and that have been adjusted by another pre-defined cross-scan coefficient to create a filtered data set that has been filtered in the cross-scan dimension of the optical beam.

38. A method according to claim 37, wherein said filtering comprises filtering the data set of a respective scan in the cross-scan dimension of the optical beam based on a plurality of data sets corresponding to scans of the workpiece occurring prior to and after the respective scan.

39. A method according to claim 38, wherein said adding comprises adding individual data points of the data set of the respective scan to corresponding individual data points of the plurality of data sets corresponding to scans of the workpiece occurring prior to and after the respective scan to thereby filter the data set of the respective scan in the cross-scan dimension of the optical beam.

40. A method according to claim 37, wherein said illuminating further comprises illuminating the workpiece with an optical beam having a predetermined Gaussian light intensity distribution such that portions of the workpiece located in a middle portion of a scan are illuminated with light having greater intensity than portions of the workpiece located on opposed end portions of the scan.

41. A method according to claim 40, wherein said generating comprises generating an adjusted data set for the scan that accounts for the predetermined Gaussian light intensity distribution of the optical beam, wherein said multiplying comprises multiplying the individual data points of a data set by a predefined cross-scan coefficient that accounts for the differences in the magnitude of light that illuminates the different positions of the workpiece in the cross-scan dimension.

42. A method according to claim 41, wherein said filtering comprises filtering the data set of the respective scan in the cross-scan dimension of the optical beam based on a plurality of data sets corresponding to scans of the workpiece occurring prior to and after the respective scan, wherein said multiplying comprises multiplying the individual data points of the data sets corresponding to scans occurring closer in time to the respective scan with greater cross-scan coefficient values than the individual data points of the data sets corresponding to scans occurring further in time from the respective scan, and wherein said adding comprises adding the corresponding individual data points of the plurality of adjusted data sets corresponding to scans of the workpiece occurring prior to and after the respective scan to the individual data points of the adjusted data set of the respective scan.

43. A method according to claim 37 further comprising filtering the optical signals received during a respective scan in the in-scan dimension of the optical beam.

44. A method according to claim 43, wherein said filtering in the in-scan dimension comprises generating an adjusted optical signal that accounts for the predetermined light intensity distribution of the optical beam in the in-scan dimension.

45. A method according to claim 44, wherein said illuminating comprises illuminating the workpiece with an optical beam having a predetermined Gaussian light intensity distribution, such that portions of the workpiece located in a middle portion of a scan are illuminated with light having greater intensity than portions of the workpiece located on opposed end portions of the scan, and wherein said generating comprises generating an adjusted signal for the scan that accounts for the predetermined Gaussian light intensity distribution of the optical beam in the in-scan dimension.

46. A method according to claim 37 further comprising removing optical noise in a scan caused by irregularities in a surface of the workpiece, wherein said removing comprises:
   receiving a data set for each respective scan that has individual data points representing the optical beam reflected from the workpiece at different positions along the scan direction;
   selecting a predetermined number of data points from each of a plurality of respective scans;
   generating an average scan having individual data points representing the average optical beam reflected from the workpiece at different positions along the scan direction for the plurality of scans; and
   subtracting the individual data points of the average scan from the respective individual data bit of each data set for each of the plurality of scans, thereby correcting each data set for irregularities in the surface of the workpiece.

47. A method according to claim 37 further comprising determining whether the workpiece contains a defect, wherein said determining comprises:
- receiving a data set for each respective scan that has individual data points representing the optical beam reflected from the workpiece at different positions along the scan direction;
- comparing each data point of the scan to a threshold value; and
- identifying portions of the workpiece that have corresponding data points in the scan that are at least as great as the threshold value as potential defects in the workpiece.

48. A method according to claim 37 further comprising compensating for consistent variations in the intensity of the optical signal, said compensating comprising:
- receiving a data set for each respective scan that has individual data points representing the optical beam reflected from the workpiece at different positions along the scan direction; and
- subtracting from the data set a signature data set having individual data points representing the consistent variations in the intensity of the optical signal.

* * * * *

UNITED STATES PATENT AND TRADEMARK OFFICE
CERTIFICATE OF CORRECTION

PATENT NO. : 6,529,270 B1
DATED : March 4, 2003
INVENTOR(S) : Bills

It is certified that error appears in the above-identified patent and that said Letters Patent is hereby corrected as shown below:

Column 18,
Line 66, "The" should read -- the --.

Column 19,
Line 14, "or" should read -- of --.

Signed and Sealed this

Twenty-second Day of July, 2003

JAMES E. ROGAN
*Director of the United States Patent and Trademark Office*